US009688587B2

(12) United States Patent
Schoenfeldt et al.

(10) Patent No.: US 9,688,587 B2
(45) Date of Patent: *Jun. 27, 2017

(54) PROCESS FOR OXYGENATE TO OLEFIN CONVERSION USING 2-D PENTASIL ZEOLITE

(71) Applicant: UOP LLC, Des Plaines, IL (US)

(72) Inventors: Nicholas J. Schoenfeldt, Chicago, IL (US); Jaime G. Moscoso, Mount Prospect, IL (US); Deng-Yang Jan, Elk Grove Village, IL (US)

(73) Assignee: UOP LLC, Des Plaines, IL (US)

( * ) Notice: Subject to any disclaimer, the term of this patent is extended or adjusted under 35 U.S.C. 154(b) by 129 days.

This patent is subject to a terminal disclaimer.

(21) Appl. No.: 14/636,798

(22) Filed: Mar. 3, 2015

(65) Prior Publication Data

US 2016/0257624 A1    Sep. 8, 2016

(51) Int. Cl.

| C07C 1/20 | (2006.01) |
| *B01J 29/40* | (2006.01) |
| *B01J 29/90* | (2006.01) |
| *C07C 4/02* | (2006.01) |
| *C07C 6/04* | (2006.01) |
| *C10G 11/00* | (2006.01) |
| *C01B 39/36* | (2006.01) |
| *B01J 35/00* | (2006.01) |
| *B01J 35/02* | (2006.01) |
| *B01J 35/10* | (2006.01) |

(52) U.S. Cl.
CPC ............. *C07C 1/20* (2013.01); *B01J 29/40* (2013.01); *B01J 29/90* (2013.01); *B01J 35/002* (2013.01); *B01J 35/023* (2013.01); *B01J 35/1057* (2013.01); *B01J 35/1061* (2013.01); *C01B 39/36* (2013.01); *C07C 4/02* (2013.01); *C07C 6/04* (2013.01); *C10G 11/00* (2013.01); *B01J 2229/186* (2013.01); *B01J 2229/42* (2013.01); *C07C 2529/40* (2013.01); *Y02P 20/52* (2015.11); *Y02P 20/584* (2015.11); *Y02P 30/42* (2015.11)

(58) Field of Classification Search
None
See application file for complete search history.

(56) References Cited

U.S. PATENT DOCUMENTS

| 3,996,305 A | 12/1976 | Berger |
| 4,341,914 A | 7/1982 | Berger |
| 4,642,406 A | 2/1987 | Schmidt |
| 4,939,110 A | 7/1990 | Sachtler |
| 5,157,183 A | 10/1992 | Cotterman |
| 5,417,844 A | 5/1995 | Boitiaux |
| 5,981,817 A | 11/1999 | Kao |
| 6,143,941 A | 11/2000 | Sharma |
| 6,180,550 B1 | 1/2001 | Beck |
| 6,303,839 B1 | 10/2001 | Marker |
| 6,355,853 B1 | 3/2002 | Sharma |
| 6,858,129 B2 | 2/2005 | Mohr |
| 7,317,133 B2 | 1/2008 | Vora |
| 7,425,660 B2 | 9/2008 | Larson |
| 7,939,701 B2 | 5/2011 | Whitchurch |
| 8,030,239 B2 | 10/2011 | Oh |
| 8,134,037 B2 | 3/2012 | Bogdan |
| 8,273,935 B2 | 9/2012 | Rekoske |
| 8,574,542 B2 | 11/2013 | Domokos |
| 8,692,044 B2 | 4/2014 | Ou |
| 8,697,929 B2 | 4/2014 | Ou |
| 8,889,937 B2 | 11/2014 | Haizmann |
| 8,889,940 B2 | 11/2014 | Bogdan |
| 2004/0182744 A1* | 9/2004 | Jan .................... C01B 39/026 208/111.01 |
| 2007/0060778 A1 | 3/2007 | Bogdan |
| 2008/0146859 A1 | 6/2008 | Rekoske |

FOREIGN PATENT DOCUMENTS

| WO | 035626 A1 | 3/2014 |
| WO | 150875 A1 | 9/2014 |

OTHER PUBLICATIONS

U.S. Appl. No. 14/636,541, filed Mar. 3, 2015, Kuzmanich.
U.S. Appl. No. 14/636,624, filed Mar. 3, 2015, Kuzmanich.
U.S. Appl. No. 14/636,672, filed Mar. 3, 2015, Moscoso.
U.S. Appl. No. 14/636,898, filed Mar. 3, 2015, Moscoso.
U.S. Appl. No. 14/636,718, filed Mar. 3, 2015, Jan.
Raj, "Selective Formation of 1,2,4 Isomer among Trimethylbenzenes in the Methylation of Xylenes over Al—Ga-, and Fe-Silicates with MEL Structure" Journal of Catalysis, V. 138, pp. 518-524, Dec. 1992, ISSN 0021-9517, Academic Press.
Reddy, "Synthesis, Characterization, and Catalytic Properties of Metallo-Titanium Silicate Molecular Sieves with MEL Topology" Journal of Catalysis, 145, 1994, pp. 73-78.
Raj, "Catalytic Properties of [Al], [Ga], and [Fe]-silicate Analogs of ZSM-11 in C7 and C8 Aromatic Hydrocarbon Reactions: Influence of Isomorphous Substitution" Proc. Int. Zeolite Conf., 9th, 1993, 2, pp. 551-558.
Ahn, "Tailoring Mesoscopically Structured H-ZSM5 Zeolites for Toluene Methylation" Journal of Catalysis, 2014, pp. 271-280.
John, "Zeolite Containing Catalysts for the Conversion of C8-aromatics Fractions" Catalysis Today, 49, 1999 Elsevier Science B.V., pp. 211-220.
Harrison, "Some Sorptive and Catalytic Properties of Zeolite Nu-10" Zeolites, Jan. 1987, vol. 7, pp. 28-34.

* cited by examiner

*Primary Examiner* — Tam M Nguyen

(57) ABSTRACT

A process for the conversion of oxygenates to olefins is presented. The process utilizes a catalyst having a 2-dimensional morphology, and the catalyst is a pentasil zeolite. The process is an oxygenate to olefins conversion under typical temperatures and pressures, but provides for an increased propylene yield and a reduced ethylene yield.

19 Claims, No Drawings

PROCESS FOR OXYGENATE TO OLEFIN CONVERSION USING 2-D PENTASIL ZEOLITE

FIELD OF THE INVENTION

The present invention relates to a new family of aluminosilicate zeolites, having a layered pentasil structure. This family of zeolites are pentasil similar to MFI/MEL type zeolites, and is characterized by unique x-ray diffraction patterns and compositions and have catalytic properties for carrying out oxygenate to olefin conversion processes.

BACKGROUND

Zeolites are crystalline aluminosilicate compositions which are microporous and which are formed from corner sharing $AlO_2$ and $SiO_2$ tetrahedra. Numerous zeolites, both naturally occurring and synthetically prepared, are used in various industrial processes. Synthetic zeolites are prepared via hydrothermal synthesis employing suitable sources of Si, Al and structure directing agents such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. Zeolites can be used as catalysts for hydrocarbon conversion reactions, which can take place on outside surfaces as well as on internal surfaces within the pore.

One particular zeolitic material, classified as ZSM-5, is disclosed in Beck, et al., U.S. Pat. No. 6,180,550, issued on Jan. 30, 2001. The zeolite comprises a synthetic porous crystalline material having a composition involving the molar relationship:

$$X_2O_3:(n)YO_2,$$

wherein X is a trivalent element, such as aluminum, boron, iron and/or gallium, preferably aluminum; Y is a tetravalent element such as silicon and/or germanium, preferably silicon; and n is less than 25, and wherein the slope of the nitrogen sorption isotherm of the material at a partial pressure of nitrogen of 0.4 to 0.7 and a temperature of 77° K is greater than 30.

While there are many types of zeolites, new zeolites provide for improved reaction conditions in the conversion of lower value hydrocarbon streams to higher value hydrocarbon products.

SUMMARY

A first embodiment of the invention is a process for the conversion of oxygenates to olefins comprising passing an oxygenate feedstream to an oxygenate conversion reactor operated at oxygenate conversion reaction conditions, wherein the reactor includes a catalyst having an layered pentasil zeolite, to generate a process stream comprising olefins, wherein the catalyst is a zeolite having a microporous crystalline structure comprising a framework of $AlO_2$ and $SiO_2$ tetrahedral units, and an empirical composition in the as synthesized and anhydrous basis expressed by the empirical formula of $M_m^{n+}R_r^{p+}AlSi_yO_z$ where M is at least one exchangeable cation selected from the group consisting of alkali and alkaline earth metals, "m" is the mole ratio of M to Al and varies from 0 to 3, R is at least one organoammonium cation selected from the group consisting of quaternary ammonium cations, diquaternary ammonium cations, "r" is the mole ratio of R to Al and has a value of about 0.1 to about 30, "n" is the weight average valence of M and has a value of about 1 to about 2, "p" is the weighted average valence of R and has a value of about 1 to about 2, "y" is the mole ratio of Si to Al and varies from greater than 32 to about 200 and "z" is the mole ratio of O to Al and has a value determined by the equation $z=(m \cdot n + r \cdot p + 3 + 4 \cdot y)/2$. An embodiment of the invention is one, any or all of prior embodiments in this paragraph up through the first embodiment in this paragraph wherein the zeolite is further characterized in that it has the x-ray diffraction pattern having at least the d spacing and intensities set forth in the following Table A:

TABLE A

| 2Θ | d (Å) | I/Io |
|---|---|---|
| 7.92-7.99 | 11.04-11.31 | m |
| 8.79-8.88 | 9.94-11.09 | m |
| 20.28-20.56 | 4.31-4.35 | w |
| 23.10-23.18 | 3.83-3.84 | vs |
| 23.86-24.05 | 3.69-3.72 | m |
| 29.90-30.05 | 2.97-2.98 | w |
| 45.02-45.17 | 2.00-2.01 | w |

An embodiment of the invention is one, any or all of prior embodiments in this paragraph up through the first embodiment in this paragraph wherein the zeolite has a mesopore surface area between 140 m²/g and 400 m²/g. An embodiment of the invention is one, any or all of prior embodiments in this paragraph up through the first embodiment in this paragraph wherein the zeolite further comprises a microporous crystalline structure comprising a framework of $AlO_2$ and $SiO_2$ tetrahedral units, further including the element E and having the empirical composition in the as synthesized and anhydrous basis expressed by the empirical formula of 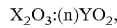$M_m^{n+}R_r^{p+}Al_{1-x}E_xSi_yO_z$ where "m" is the mole ratio of M to (Al+E) and varies from 0 to 3, "r" is the mole ratio of R to (Al+E) and has a value of about 0.1 to about 30, E is an element selected from the group consisting of gallium, iron, boron, indium and mixtures thereof, "x" is the mole fraction of E and has a value from 0 to 1.0, "y" is the mole ratio of Si to (Al+E) and varies from greater than 32 to about 200 and "z" is the mole ratio of O to (Al+E) and has a value determined by the equation $z=(m \cdot n + r \cdot p + 3 + 4 \cdot y)/2$. An embodiment of the invention is one, any or all of prior embodiments in this paragraph up through the first embodiment in this paragraph further comprising separating the process stream into an ethylene stream, a propylene stream, a $C_4$ stream, a $C_5$ stream, and a $C_{5+}$ heavies stream, or some combination thereof. An embodiment of the invention is one, any or all of prior embodiments in this paragraph up through the first embodiment in this paragraph further comprising passing the heavies stream, comprising $C_4$ and/or $C_{4+}$ olefins, to an olefin cracking unit, or to a metathesis unit along with some portion or all of the ethylene stream. An embodiment of the invention is one, any or all of prior embodiments in this paragraph up through the first embodiment in this paragraph wherein the oxygenates comprise alcohols, aldehydes, ethers and mixtures thereof. An embodiment of the invention is one, any or all of prior embodiments in this paragraph up through the first embodiment in this paragraph wherein the oxygenate comprises methanol. An embodiment of the invention is one, any or all of prior embodiments in this paragraph up through the first embodiment in this paragraph wherein oxygenate conversion reactor comprises a fluidized reactor bed, and wherein the oxygenate conversion reactor generate an effluent stream comprising catalyst and a process fluid, wherein the effluent stream is separated into a spent catalyst stream and the process stream comprising olefins. An embodiment of the invention is one, any or all of prior embodiments in this paragraph up through the first embodiment in this paragraph wherein the catalyst stream is passed to a regenerator to generate a regenerated catalyst stream. An embodiment of the invention is one, any or all of prior embodiments in this paragraph up through the first embodiment in this paragraph further comprising passing the regenerated catalyst stream to a stripper, to generate a stripped catalyst stream comprising catalyst with carbon oxides removed. An embodiment of the invention is one, any or all of prior embodiments in this paragraph up through the first embodiment in this paragraph further comprising passing the stripped catalyst stream to oxygenate conversion reactor. An embodiment of the invention is one, any or all of prior embodiments in this paragraph up through the first embodiment in this paragraph wherein the oxygenate conversion reaction conditions include a temperature in the range from 300° C. to 600° C. An embodiment of the invention is one, any or all of prior embodiments in this paragraph up through the first embodiment in this paragraph wherein the oxygenate conversion reaction conditions include a pressure which allows an absolute oxygenate partial pressure in the range from 100 kPa to 800 kPa.

A second embodiment of the invention is a process for the conversion of oxygenates to olefins comprising passing an oxygenate feedstream to an oxygenate conversion reactor operated at oxygenate conversion reaction conditions, wherein the reactor includes a catalyst having an layered pentasil MFI/MEL structure, to generate a process stream comprising olefins, wherein the catalyst is a zeolite of claim 1 having a microporous crystalline structure comprising a framework of $AlO_2$ and $SiO_2$ tetrahedral units, further including the element E and having the empirical composition in the as synthesized and anhydrous basis expressed by the empirical formula of $M_m^{n+}R_r^{p+}Al_{1-x}E_xSi_yO_z$; wherein m" is the mole ratio of M to (Al+E) and varies from 0 to 1, "r" is the mole ratio of R to (Al+E) and has a value of 0.1 to about 30, "n" is the weight average valence of M and has a value of 1 to 2, "p" is the weighted average valence of R and has a value of 1 to 2, "x" is the mole fraction of E and has a value from 0 to 1.0, "y" is the mole ratio of Si to (Al+E) and varies from greater than 32 to about 200 and "z" is the mole ratio of O to (Al+E) and has a value determined by the equation $z=(m\cdot n+r\cdot p+3+4\cdot y)/2$ and it is characterized in that it has the x-ray diffraction pattern having at least the d spacing and intensities set forth in the following Table A:

TABLE A

| 2Θ | d (Å) | I/Io |
| --- | --- | --- |
| 7.92-7.99 | 11.04-11.31 | m |
| 8.79-8.88 | 9.94-11.09 | m |
| 20.28-20.56 | 4.31-4.35 | w |
| 23.10-23.18 | 3.83-3.84 | vs |

TABLE A-continued

| 2Θ | d (Å) | I/Io |
| --- | --- | --- |
| 23.86-24.05 | 3.69-3.72 | m |
| 29.90-30.05 | 2.97-2.98 | w |
| 45.02-45.17 | 2.00-2.01 | w |

An embodiment of the invention is one, any or all of prior embodiments in this paragraph up through the second embodiment in this paragraph wherein the oxygenate conversion reaction conditions include a temperature in the range from 300° C. to 600° C. An embodiment of the invention is one, any or all of prior embodiments in this paragraph up through the second embodiment in this paragraph wherein the oxygenate conversion reaction conditions include a pressure which allows an absolute oxygenate partial pressure in the range from 100 kPa to 800 kPa. An embodiment of the invention is one, any or all of prior embodiments in this paragraph up through the second embodiment in this paragraph further comprising separating the process stream into an ethylene stream, a propylene stream, a $C_4$ stream, a $C_5$ stream, and a $C_{5+}$ heavies stream, or some combination thereof. An embodiment of the invention is one, any or all of prior embodiments in this paragraph up through the second embodiment in this paragraph further comprising passing the heavies stream, comprising the $C_4$ and/or $C_4+$ olefins, to an olefin cracking unit, or to a metathesis unit along with some portion or all of the ethylene stream. An embodiment of the invention is one, any or all of prior embodiments in this paragraph up through the second embodiment in this paragraph wherein the oxygenates comprises methanol.

Other objects, advantages and applications of the present invention will become apparent to those skilled in the art from the following detailed description.

DETAILED DESCRIPTION

A new family of zeolitic materials has been successfully prepared. The new material is a pentasil zeolite and is unique as determined by its x-ray diffraction spectrum. The structure is related to MFI/MEL pentasil class of zeolite framework types, and as a 2-dimensional layered structure.

New zeolites can have properties that produce unexpected results that lead to important economies in conversion processes. The methods of making zeolites can be similar, but control parameters and choices of chemicals for the templates can control the structure of the zeolites. This new zeolite has a small crystallite size. Typically, the approach for producing zeolites with an MFI/MEL structure and with a high surface area, arises when the process of synthesis uses the Charge Density Mismatch Approach to zeolite synthesis (as shown in U.S. Pat. No. 7,578,993). The zeolite has a $Si/Al_2$ ratios of greater than about 50. The present invention provides for a high surface area MFI/MEL layer pentasil zeolite.

The microporous crystalline zeolite is prepared by a hydrothermal crystallization of a reaction mixture prepared by combining reactive sources of M, R, aluminum, silicon and optionally E. The sources of aluminum include but are not limited to aluminum alkoxides, precipitated aluminas, aluminum metal, aluminum salts and alumina sols. Specific examples of aluminum alkoxides include, but are not limited to aluminum ortho sec-butoxide and aluminum ortho isopropoxide. Sources of silica include but are not limited to tetraethylorthosilicate, colloidal silica, precipitated silica and alkali silicates. Sources of the E elements include but are not limited to alkali borates, boric acid, precipitated gallium oxyhydroxide, gallium sulfate, ferric sulfate, and ferric chloride. Sources of the M metals, potassium and sodium, include the halide salts, nitrate salts, acetate salts, and hydroxides of the respective alkali metals. R is an organoammonium cation selected from the group consisting tetrabutylammonium (TBA), tetrabutylphosphonium (TBP) and mixtures thereof, and the sources include the hydroxide, chloride, bromide, iodide and fluoride compounds. Specific examples include without limitation tetrabutylammonium hydroxide, tetrabutylammonium chloride, tetrabutylammonium bromide, tetrabutylphosphonium hydroxide, tetrabutylphosphonium chloride, and tetrabutylphosphonium bromide.

One conversion process of increasing industrial importance it the methanol to olefins process. The methanol to olefins (MTO) process is a growth area, and primarily utilizes a catalyst having a chabazite type 3-D structure. The catalyst is highly selective to ethylene and propylene, but deactivate relatively quickly due to coke formation. An MTO process with this type of catalyst requires a fluidized bed reactor system with a quick recycling of the catalyst between the reactor and regenerator.

The present invention is a process for the conversion of oxygenates to olefins. The process includes passing an oxygenate feedstream to an oxygenate conversion reactor. The reactor is operated at oxygenate conversion reaction conditions, which includes an oxygenate conversion catalyst, to generate a process stream comprising olefins. The oxygenate conversion catalyst is a layered pentasil zeolite, that has a microporous crystalline structure comprising a framework of $AlO_2$ and $SiO_2$ tetrahedral units. The zeolite has an empirical composition in the as synthesized and anhydrous basis expressed by the empirical formula of:

$$M_m^{n+}R_r^{p+}AlSi_yO_z.$$

In the formula, M is at least one exchangeable cation selected from the group consisting of alkali and alkaline earth metals, "m" is the mole ratio of M to Al and varies from 0 to 3, R is at least one organoammonium cation selected from the group consisting of quaternary ammonium cations, diquaternary ammonium cations, "r" is the mole ratio of R to Al and has a value of about 0.1 to about 30, "n" is the weight average valence of M and has a value of about 1 to about 2, "p" is the weighted average valence of R and has a value of about 1 to about 2, "y" is the mole ratio of Si to Al and varies from greater than 32 to about 200 and "z" is the mole ratio of 0 to A. The value of "z" is determined by the equation:

$$z=(m \cdot n+r \cdot p+3+4 \cdot y)/2.$$

The zeolite used in the process can be further characterized by the x-ray diffraction pattern having at least the d spacing and intensities set forth in Table A:

TABLE A

| 2Θ | d (Å) | I/Io |
|---|---|---|
| 7.92-7.99 | 11.04-11.31 | m |
| 8.79-8.88 | 9.94-11.09 | m |
| 20.28-20.56 | 4.31-4.35 | w |
| 23.10-23.18 | 3.83-3.84 | vs |
| 23.86-24.05 | 3.69-3.72 | m |
| 29.90-30.05 | 2.97-2.98 | w |
| 45.02-45.17 | 2.00-2.01 | w |

The zeolite has a large surface area, and has a mesopore surface area between 140 m²/g and 400 m²/g.

In one embodiment, the process includes a zeolite catalyst further including the element E, wherein E comprises one or more elements from gallium, iron, boron and indium. In this embodiment, the zeolite comprises a microporous crystalline structure comprising a framework of $AlO_2$ and $SiO_2$ tetrahedral units, and having the empirical composition in the as synthesized and anhydrous basis expressed by the empirical formula of:

$$M_m^{n+}R_r^{p+}Al_{1-x}E_xSi_yO_z$$

where "m" is the mole ratio of M to (Al+E) and varies from 0 to 3, "r" is the mole ratio of R to (Al+E) and has a value of about 0.1 to about 30, "x" is the mole fraction of E and has a value from 0 to 1.0, "y" is the mole ratio of Si to (Al+E) and varies from greater than 32 to about 200. In this formula, "z" is the mole ratio of 0 to (Al+E) and has a value determined by the equation:

$$z=(m \cdot n+r \cdot p+3+4 \cdot y)/2.$$

The oxygenate conversion reaction conditions include a temperature in the range from 300° C. to 600° C. The oxygenate conversion reaction conditions further include a pressure which allows an absolute oxygenate partial pressure in the range from 100 kPa to 800 kPa.

The process further includes passing the process stream to a light olefins separation unit, wherein the separation unit generates an ethylene stream, a propylene stream, a $C_4$ stream, a $C_5$ stream, and a $C_{5+}$ heavies stream, or some combination thereof. The present invention provides for the conversion of oxygenates to olefins with an increased portion of the conversion to heavier olefins. This provides for a shift to increase the amount of propylene generated.

The process can further include passing a heavies stream comprising the $C_4$ stream, the $C_5$ stream, and the $C_{5+}$ stream, to an olefin cracking unit to generate an olefin cracking effluent stream comprising ethylene and propylene, thereby further increasing the ethylene and propylene yield in the process.

The oxygenates in the oxygenate feedstream can include alcohols, aldehydes, ethers, and mixtures thereof. A common oxygenate for conversion is methanol.

In another embodiment, the process can include passing the $C_4$ stream and/or a $C_4^+$ stream along with a portion of, or all of, the ethylene stream to a metathesis reactor. The metathesis reactor is operate at metathesis reaction conditions with a metathesis catalyst to convert a metathesis feedstream comprising ethylene and butylenes, or ethylene and a mixture of higher olefins such as butylenes and pentenes, to an effluent stream comprising propylene, or a combination of propylene and butylenes. The effluent stream is passed to the light olefin recovery unit to separation the propylene into the propylene stream.

The process can operate the oxygenate conversion reactor as a fixed bed reactor or a fluidized bed reactor. When the reactor is a fluidized bed reactor, the reactor generates an effluent stream comprising catalyst and the process fluid comprising light olefins. The effluent stream is separated into a spent catalyst stream and the process stream comprising olefins. The catalyst stream is passed to a regenerator to generate a regenerated catalyst stream.

The regenerated catalyst stream can be passed to a stripper, to generate a stripped catalyst stream comprising catalyst with carbon oxides removed. And the stripped catalyst stream is passed back to the oxygenate conversion reactor.

The new catalyst has displayed a high propylene selectivity, of between 47% and 52% and has an uncharacteristically low ethylene selectivity of between 3% and 6%. Typical MFI catalysts can reach similar, but lower, propylene selectivity, between 40% and 45%, but often display elevated ethylene selectivity of between 10% and 20%. The unique and novel features of this catalyst allows for high propylene and low ethylene selectivity. This appears to result from the unique catalyst morphology, having a 2-dimensional crystal morphology rather than the typical 3-D morphology. This 2D crystal lattice appears to allow altered diffusion properties, which may affect the reaction mechanism leading to highly selective propylene formation without the production of high levels of ethylene.

EXAMPLES

Example 1

Layered Pentasil 1

An aluminosilicate reaction solution was prepared by first mixing 13.15 g of aluminum tri-sec-butoxide (95+%), 777.62 g tetrabutylammonium hydroxide (55 mass-% solution), and 700 g of ice water mixture while stirring vigorously. After thorough mixing, 1167.98 g tetraethyl orthosilicate was added. The reaction mixture was homogenized for an additional hour with a high speed mechanical stirrer. A composite aqueous solution containing 2.75 g of NaOH dissolved in 137.7 g distilled water was added, drop-wise, to the aluminosilicate solution. After the addition was completed, the resulting reaction mixture was homogenized for 1 hour, transferred to a 2000 ml Parr stainless steel autoclave which was heated to 115° C. and maintained at that temperature for 59 hrs. The solid product was recovered by centrifugation, washed with de-ionized water, and dried at 80° C.

The product was identified as a pentasil zeolite by powder x-ray diffraction. Representative diffraction lines observed for the product are shown in Table 1. The product composition was determined by elemental analysis to consist of the following mole ratios: Si/Al=59.8, Na/Al=0.82. A portion of the material was calcined by ramping to 560° C. for 5 hours followed by an 8 hour dwell in air. The BET surface area was 697 m$^2$/g, the micropore area was 474 m$^2$/g, the mesopore area was 223 m$^2$/g, the micropore volume was 0.253 cc/g, and mesopore volume was 0.953 cc/g. Scanning Electron Microscopy (SEM) revealed clusters of nano spheres of less than 20 nm. Chemical analysis was as follows: 0.74% Al, 46.0% Si, and 0.52% Na, Na/Al=0.82, Si/Al$_2$=119.

TABLE 1

| 2θ | d (Å) | I/I$_0$ % |
|---|---|---|
| 7.92 | 11.15 | m |
| 8.8 | 10.04 | m |
| 20.38 | 4.35 | w |
| 23.13 | 3.84 | vs |
| 23.98 | 3.7 | m |
| 29.96 | 2.98 | w |
| 45.14 | 2.00 | w |

The pentasil zeolite of example 1 was calcined at 560° C. for 8 hours under nitrogen and then under air. The pentasil layer zeolite was then ammonium ion exchanged to exchange Na for NH$_4^+$ by contacting 500 ml of 1 M NH$_4$NO$_3$ solution with 40 g of calcined pentasil layered zeolite at 80° C. and stirring for 1 hour. The product was then filtered and washed. The procedure was repeated three times. The final sodium level was 0.002%. The pentasil layer zeolite was then calcined at 550° C. in air for 2 h to convert NH$_4^+$ to H$^+$ by loss of ammonia.

Example 2

Layered Pentasil 2

An aluminosilicate reaction solution was prepared by first mixing 13.87 g of aluminum tri-sec-butoxide (95+%), 386.39 g tetrabutylammonium hydroxide (55 mass-% solution), and 300 g of ice water mixture while stirring vigorously. After thorough mixing, 580.35 g tetraethyl orthosilicate was added. The reaction mixture was homogenized for an additional hour with a high speed mechanical stirrer. A composite aqueous solution containing 2.73 g of NaOH dissolved in 116.67 g distilled water was added, drop-wise, to the aluminosilicate solution. After the addition was completed, the resulting reaction mixture was homogenized for 1 hour, transferred to a 2000 ml Parr stainless steel autoclave which was heated to 115° C. and maintained at that temperature for 57 hrs. The solid product was recovered by centrifugation, washed with de-ionized water, and dried at 80° C.

The product was identified as a pentasil zeolite by powder x-ray diffraction. Representative diffraction lines observed for the product are shown in Table 2. The product composition was determined by elemental analysis to consist of the following mole ratios: Si/Al=24.9, Na/Al=0.92. A portion of the material was calcined by ramping to 560° C. for 5 hours followed by a 8 hour dwell in air. The BET surface area was 517 m$^2$/g, the micropore area was 258 m$^2$/g, the mesopore area was 259 m$^2$/g, the micropore volume was 0.135 cc/g, and mesopore volume was 0.94 cc/g. Scanning Electron Microscopy (SEM) revealed clusters of nano spheres of less than 20 nm. Chemical analysis was as follows: 1.73% Al, 44.9% Si, and 1.37% Na, Na/Al=0.93, Si/Al$_2$=49.8.

TABLE 2

| 2θ | d (Å) | I/I$_0$ % |
|---|---|---|
| 7.94 | 11.12 | m |
| 8.79 | 10.04 | m |
| 20.38 | 4.35 | w |
| 23.16 | 3.83 | vs |
| 23.86 | 3.72 | m |
| 29.96 | 2.98 | w |
| 45.07 | 2.00 | w |

The pentasil zeolite of example 2 was calcined at 560° C. for 8 hours under nitrogen and then under air. The pentasil layer zeolite was then ammonium ion exchanged to exchange Na for NH$_4^+$ by contacting 500 ml of 1 M NH$_4$NO$_3$ solution with 10 g of calcined pentasil layered zeolite at 80° C. and stirring for 1 hour. The product was then filtered and washed. The procedure was repeated three times. The final sodium level was 0.07%. The pentasil layer zeolite was then calcined at 550° C. in air for 2 h to convert NH$_4^+$ to H$^+$ by loss of ammonia Example 3

Layered Pentasil 3

An aluminosilicate reaction solution was prepared by first mixing 13.82 g of aluminum tri-sec-butoxide (95+%), 1126.74 g tetrabutylammonium hydroxide (55 mass-% solution), and 400 g of ice water mixture while stirring vigorously. After thorough mixing, 1156.66 g tetraethyl orthosilicate was added. The reaction mixture was homogenized for an additional hour with a high speed mechanical stirrer. A composite aqueous solution containing 2.72 g of NaOH dissolved in 100.0 g distilled water was added, drop-wise, to the aluminosilicate solution. After the addition was completed, the resulting reaction mixture was homogenized for 1 hour, transferred to a 2000 ml Parr stainless steel autoclave which was heated to 115° C. and maintained at that temperature for 48 hrs. The solid product was recovered by centrifugation, washed with de-ionized water, and dried at 80° C.

The product was identified as a pentasil zeolite by powder x-ray diffraction. Representative diffraction lines observed for the product are shown in Table 3. The product composition was determined by elemental analysis to consist of the following mole ratios: Si/Al=59.8, Na/Al=0.82. A portion of the material was calcined by ramping to 560° C. for 5 hours followed by an 8 hour dwell in air. The BET surface area was 697 m$^2$/g, the micropore area was 474 m$^2$/g, the mesopore area was 223 m$^2$/g, the micropore volume was 0.253 cc/g, and mesopore volume was 0.953 cc/g. Scanning Electron Microscopy (SEM) revealed clusters of nano spheres of less than 20 nm. Chemical analysis was as follows: 0.74% Al, 46.0% Si, and 0.52% Na, Na/Al=0.82, Si/Al$_2$=119.

TABLE 3

| 2θ | d (Å) | I/I$_0$ % |
|---|---|---|
| 7.92 | 11.15 | m |
| 8.79 | 10.04 | m |
| 23.12 | 3.84 | vs |
| 23.96 | 3.71 | m |
| 29.94 | 2.98 | w |
| 45.17 | 2.00 | w |

The pentasil zeolite of example 3 was calcined at 560° C. for 8 hours under nitrogen and then under air. The pentasil layer zeolite was then ammonium ion exchanged to exchange Na for NH$_4^+$ by contacting 500 ml of 1 M NH$_4$NO$_3$ solution with 10 g of calcined pentasil layer zeolite at 80° C. and stirring for 1 hour. The product was then filtered and washed. The procedure was repeated three times. The final sodium level was 0.007%. The pentasil layer zeolite was then calcined at 550° C. in air for 2 h to convert NH$_4^+$ to H$^+$ by loss of ammonia.

Example 4

Standard Pentasil

An aluminosilicate reaction gel was prepared by first weighting 848.26 g of Ludox AS-40 colloidal silica in a 2-L beaker, then added 138.10 g of tetrapropyl ammonium bromide solution (50%) was added. A composite aqueous solution containing 33.92 g of NaOH and 25.63 g of liquid sodium aluminate in 353.37 g distilled water was added drop-wise to the silicate solution. The final gel was allowed to mix for 20 minutes. The gel was transferred to a 2-L stirred reactor and heated to 125° C. for 72 hrs at 500 RPM. The solid was separated by centrifuge and washed 3 times with water, dried and determined by XRD to be a zeolite with a MFI structure.

The product composition was determined by elemental analysis to consist of the following mole ratios: Si/Al=41.4, Na/Al=0.66. A portion of the material was calcined by ramping to 560° C. for 5 hours followed by an 8 hour dwell in air. The BET surface area was 365 m$^2$/g, the micropore area was 310 m$^2$/g, the mesopore area was 55 m$^2$/g, the micropore volume was 0.161 cc/g, and mesopore volume was 0.52 cc/g. Scanning Electron Microscopy (SEM) revealed discrete and small crystal size between 20 to 50 nm. Chemical analysis was as follows: 1.06% Al, 45.6% Si, and 0.66% Na, Na/Al=0.66, Si/Al$_2$=82.4.

The standard pentasil zeolite of example 4 was calcined at 560° C. for 8 hours under nitrogen and then under air. The standard pentasil zeolite was then ammonium ion exchanged to exchange Na for NH$_4^+$ by contacting 500 ml of 1 M NH$_4$NO$_3$ solution with 20 g of calcined standard pentasil zeolite at 80° C. and stirring for 1 hour. The product was then filtered and washed. The procedure was repeated three times. The final sodium level was 0.004%. This standard pentasil zeolite was then calcined at 550° C. in air for 2 h to convert NH$_4^+$ to H$^+$ by loss of ammonia.

Example 5

Fixed bed pilot-plant test conditions and results are as follows. A 100 wt % solution of methanol was fed from a saturator with inert carrier gas (N$_2$) with suitable process flow (135 cc/min), saturator bath temperature (23° C.), and zeolite loading (325 mg) to allow a WHSV (weight hourly space velocity) of 3.8 h$^{-1}$. The feed was then carried through a fixed bed micro-reactor maintained at atmospheric pressure to allow a 0.1 atm methanol partial pressure. Reactor temperature was controlled at 450° C. The resulting performance values at 4 hours on stream were obtained for the materials described in Examples 1-4:

| Sample | Si/Al$_2$ | Conversion | C$_2^=$ % | C$_3^=$ % | C$_3^=$/C$_2^=$ |
|---|---|---|---|---|---|
| Layered Pentasil (ex 1) | 119 | 100 | 3.4 | 48.2 | 14.2 |
| Layered Pentasil (ex 2) | 50 | 95 | 1.6 | 38.4 | 24.0 |
| Layered Pentasil (ex 3) | 130 | 100 | 5.6 | 49.5 | 8.8 |
| Standard Pentasil (ex 4) | 82 | 100 | 14.7 | 44.4 | 3.0 |

Note that selectivity values listed are all obtained at identical time on stream. Conversion is calculated to incorporate methanol and DME. Selectivity values are given as wt % component. From this data it can be observed that the use of a layered pentasil catalyst with a range of Si/Al$_2$ values allows increases in C$_3^=$/C$_2^=$ ratio compared to the standard pentasil benchmark material. Elevated C$_3^=$/C$_2^=$ ratio is currently economically favorable due to the higher demand for propylene, and propylene only formation routes from oxygenate feeds. Furthermore, the reduced ethylene formation observed with the layered pentasil catalyst would ease downstream olefin separations requirements in the process, thereby making it a more economical process.

While the invention has been described with what are presently considered the preferred embodiments, it is to be understood that the invention is not limited to the disclosed embodiments, but it is intended to cover various modifications and equivalent arrangements included within the scope of the appended claims.

What is claimed is:

1. A process for the conversion of oxygenates to olefins comprising:

passing an oxygenate feedstream to an oxygenate conversion reactor operated at oxygenate conversion reaction conditions, wherein the reactor includes a catalyst having a layered pentasil zeolite, to generate a process stream comprising olefins, wherein the catalyst is a zeolite having a microporous crystalline structure comprising a framework of $AlO_2$ and $SiO_2$ tetrahedral units, and an empirical composition in the as synthesized and anhydrous basis expressed by the empirical formula of:

$$M_m^{n+}R_r^{p+}AlSi_yO_z$$

where M is at least one exchangeable cation selected from the group consisting of alkali and alkaline earth metals, "m" is the mole ratio of M to Al and varies from 0 to 3, R is at least one organoammonium cation selected from the group consisting of quaternary ammonium cations, diquaternary ammonium cations, "r" is the mole ratio of R to Al and has a value of about 0.1 to about 30, "n" is the weight average valence of M and has a value of about 1 to about 2, "p" is the weighted average valence of R and has a value of about 1 to about 2, "y" is the mole ratio of Si to Al and varies from greater than 32 to about 200 and "z" is the mole ratio of O to Al and has a value determined by the equation:

$$z=(m \cdot n + r \cdot p + 3 + 4 \cdot y)/2; \text{ and}$$

wherein the zeolite is further characterized in that it has the x-ray diffraction pattern having at least the d spacing and intensities set forth in the following Table:

TABLE

| 2Θ | d (Å) | I/Io |
|---|---|---|
| 7.92-7.99 | 11.04-11.31 | m |
| 8.79-8.88 | 9.94-11.09 | m |
| 20.28-20.56 | 4.31-4.35 | w |
| 23.10-23.18 | 3.83-3.84 | vs |
| 23.86-24.05 | 3.69-3.72 | m |
| 29.90-30.05 | 2.97-2.98 | w |
| 45.02-45.17 | 2.00-2.01 | w. |

2. The process of claim 1 wherein the zeolite has a mesopore surface area between 140 m²/g and 400 m²/g.

3. The process of claim 1 wherein the zeolite further comprises a microporous crystalline structure comprising a framework of $AlO_2$ and $SiO_2$ tetrahedral units, further including the element E and having the empirical composition in the as synthesized and anhydrous basis expressed by the empirical formula of:

$$M_m^{n+}R_r^{p+}Al_{1-x}E_xSi_yO_z$$

where "m" is the mole ratio of M to (Al+E) and varies from 0 to 3, "r" is the mole ratio of R to (Al+E) and has a value of about 0.1 to about 30, E is an element selected from the group consisting of gallium, iron, boron, indium and mixtures thereof, "x" is the mole fraction of E and has a value from 0 to 1.0, "y" is the mole ratio of Si to (Al+E) and varies from greater than 32 to about 200 and "z" is the mole ratio of O to (Al+E) and has a value determined by the equation:

$$z=(m \cdot n+r \cdot p+3+4 \cdot y)/2.$$

4. The process of claim 1 further comprising separating the process stream into an ethylene stream, a propylene stream, a $C_4$ stream, a $C_5$ stream, and a $C_{5+}$ heavies stream.

5. The process of claim 4 further comprising passing the heavies stream, comprising $C_{4+}$ olefins, to an olefin cracking unit, or to a metathesis unit.

6. The process of claim 1 wherein the oxygenates comprise alcohols, aldehydes, ethers and mixtures thereof.

7. The process of claim 6 wherein the oxygenate comprises methanol.

8. The process of claim 1 wherein oxygenate conversion reactor comprises a fluidized reactor bed, and wherein the oxygenate conversion reactor generate an effluent stream comprising catalyst and a process fluid, wherein the effluent stream is separated into a spent catalyst stream and the process stream comprising olefins.

9. The process of claim 8 wherein the catalyst stream is passed to a regenerator to generate a regenerated catalyst stream.

10. The process of claim 9 further comprising passing the regenerated catalyst stream to a stripper, to generate a stripped catalyst stream comprising catalyst with carbon oxides removed.

11. The process of claim 10 further comprising passing the stripped catalyst stream to the oxygenate conversion reactor.

12. The process of claim 1 wherein the oxygenate conversion reaction conditions include a temperature in the range from 300° C. to 600° C.

13. The process of claim 1 wherein the oxygenate conversion reaction conditions include an oxygenate partial pressure in the range from 100 kPa to 800 kPa.

14. A process for the conversion of oxygenates to olefins comprising:

passing an oxygenate feedstream to an oxygenate conversion reactor operated at oxygenate conversion reaction conditions, wherein the reactor includes a catalyst having a layered pentasil structure, to generate a process stream comprising olefins, wherein the catalyst is a zeolite having a microporous crystalline structure comprising a framework of $AlO_2$ and $SiO_2$ tetrahedral units, and having the empirical composition in the as synthesized and anhydrous basis expressed by the empirical formula of:

$$M_m^{n+}R_r^{p+}Al_{1-x}E_xSi_yO_z;$$

wherein M is at least one exchangeable cation selected from the group consisting of alkali and alkaline earth metals, m" is the mole ratio of M to (Al+E) and varies from 0 to 1, R is at least one organoammonium cation selected from the group consisting of quaternary ammonium cations, diquaternary ammonium cations, "r" is the mole ratio of R to (Al+E) and has a value of 0.1 to about 30, "n" is the weight average valence of M and has a value of 1 to 2, "p" is the weighted average valence of R and has a value of 1 to 2, E is an element selected from the group consisting of gallium, iron, boron, indium and mixtures thereof, "x" is the mole fraction of E and has a value from 0 to 1.0, "y" is the mole ratio of Si to (Al+E) and varies from greater than 32 to about 200 and "z" is the mole ratio of O to (Al+E) and has a value determined by the equation:

$$z=(m \cdot n+r \cdot p+3+4 \cdot y)/2$$

and it is characterized in that it has the x-ray diffraction pattern having at least the d spacing and intensities set forth in the following Table:

TABLE

| 2Θ | d (Å) | I/Io |
|---|---|---|
| 7.92-7.99 | 11.04-11.31 | m |
| 8.79-8.88 | 9.94-11.09 | m |
| 20.28-20.56 | 4.31-4.35 | w |
| 23.10-23.18 | 3.83-3.84 | vs |
| 23.86-24.05 | 3.69-3.72 | m |
| 29.90-30.05 | 2.97-2.98 | w |
| 45.02-45.17 | 2.00-2.01 | w. |

15. The process of claim 14 wherein the oxygenate conversion reaction conditions include a temperature in the range from 300° C. to 600° C.

16. The process of claim 14 wherein the oxygenate conversion reaction conditions include an oxygenate partial pressure in the range from 100 kPa to 800 kPa.

17. The process of claim 14 further comprising separating the process stream into an ethylene stream, a propylene stream, a $C_4$ stream, a $C_5$ stream, and a $C_{5+}$ heavies stream.

18. The process of claim 17 further comprising passing the heavies stream, comprising $C_{4+}$ olefins, to an olefin cracking unit, or a metathesis unit.

19. The process of claim 14 wherein the oxygenates comprises methanol.

* * * * *